US00PP31446P2

(12) United States Plant Patent
Vinson

(10) Patent No.: US PP31,446 P2
(45) Date of Patent: Feb. 18, 2020

(54) BLACKBERRY PLANT NAMED 'FNZ-6VB'

(50) Latin Name: ***Rubus* subg. *rubus***
Varietal Denomination: FNZ-6VB

(71) Applicant: Berry World Plus Ltd, Broxbourne (GB)

(72) Inventor: Peter Vinson, Kent (GB)

(73) Assignee: BERRY WORLD PLUS, LTD, Brox Bourne (GB)

( * ) Notice: Subject to any disclaimer, the term of this patent is extended or adjusted under 35 U.S.C. 154(b) by 0 days.

(21) Appl. No.: 16/350,869

(22) Filed: Jan. 25, 2019

(30) Foreign Application Priority Data

Jan. 26, 2018 (QZ) ..... PBR 2018/0305

(51) Int. Cl.
*A01H 5/08* (2018.01)
*A01H 6/76* (2018.01)

(52) U.S. Cl.
USPC ..... Plt./203

(58) Field of Classification Search
USPC ..... Plt./156, 203
See application file for complete search history.

(56) References Cited

PUBLICATIONS

Diario Oficial de la federaction. Jul. 1, 2019. (http://www.dof.gob.mx/nota_detalle.php?codigo=5564547.&fecha=01/07/2019). 3 pages. (Year: 2019).*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of Blackberry named 'FNZ-6VB' that is characterized by its early flowering and fruit production, its medium firm berries that are medium large in size, its 3 leaflets per leaf, its berries with flavor and quality suitable for the fresh fruit market, and its spreading growth habit.

2 Drawing Sheets

Botanical classification: *Rubus* subg. *rubus*.
Cultivar designation: 'FNZ-6VB'.

CROSS REFERENCE TO A RELATED APPLICATION

This application is co-pending with a U.S. Plant Patent Application filed for a plant derived from the same breeding program that is entitled *Rubus* Plant Named 'BWP-FNZ8VB' (U.S. Plant patent application Ser. No. 16/350,868).

BACKGROUND OF THE INVENTION

The present invention relates to a new and distinct cultivar of blackberry plant, botanically known as *Rubus* subg. *Rubus* 'FNZ-6VB' and will be referred to hereinafter by its cultivar name, 'FNZ-6VB'. 'FNZ-6VB' is a new blackberry plant grown for fruit production.

The new cultivar originated from an ongoing breeding program by the Inventor in Faversham, Kent, United Kingdom. 'FNZ-6VB' arose from a cross made between 'Waldo' (not patented) as the female parent and 'Karaka Black' as the male parent (not patented). 'FNZ-6VB' was selected as a single unique plant in from amongst the seedlings from the above cross in July of 2013.

Asexual propagation of the new cultivar was first accomplished by the Inventor by bud and cane cuttings in winter of 2013 in Faversham, Kent, United Kingdom. Asexual propagation of the new cultivar by bud and cane cuttings and tissue culture using meristem tissue has shown that the characteristics of the new cultivar are stable and reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

SUMMARY OF THE INVENTION

The following traits have been repeatedly observed and represent the characteristics of the new cultivar. These attributes in combination distinguish 'FNZ-6VB' as a new and unique cultivar of *Rubus*.

1. 'FNZ-6VB' exhibits early flowering and fruit production.
2. 'FNZ-6VB' exhibits medium firm berries that are medium large in size.
3. 'FNZ-6VB' exhibits 3 leaflets per leaf.
4. 'FNZ-6VB' exhibits berries with flavor and quality suitable for the fresh fruit market.
5. 'FNZ-6VB' exhibits a spreading growth habit.

The female parent of 'FNZ-6VB', 'Waldo', differs from 'FNZ-6VB' in having fruit that is suitable from processing but not for the fresh fruit market and in having canes that are thornless. The male parent of 'FNZ-6VB', 'Karaka Black', differs from 'FNZ-6VB' in having 7 leaflets per leaf and in having less vigor. 'FNZ-6VB' can also be compared to the cultivars 'Loch Ness' (U.S. Plant Pat. No. 6,782) and 'BWP-FNZ8VB'. 'Loch Ness' differs from 'FNZ-6VB' in having a fruiting season that is later (mid-season) and in having an upright growth habit. 'BWP-FNZ8VB' differs from 'FNZ-6VB' in having canes that are thornless and in producing flowers and fruit later in the season.

BRIEF DESCRIPTION OF THE DRAWINGS

The accompanying colored photographs illustrate the overall appearance and distinct characteristics of the new *Rubus*. The photographs were taken of a plant 2 years in age as grown in a poly tunnel in a 22-cm square container in Faversham, Kent, United Kingdom.

The photograph in FIG. 1 provides a view of a section of young canes with spines of 'FNZ-6VB'.

Figure 1:
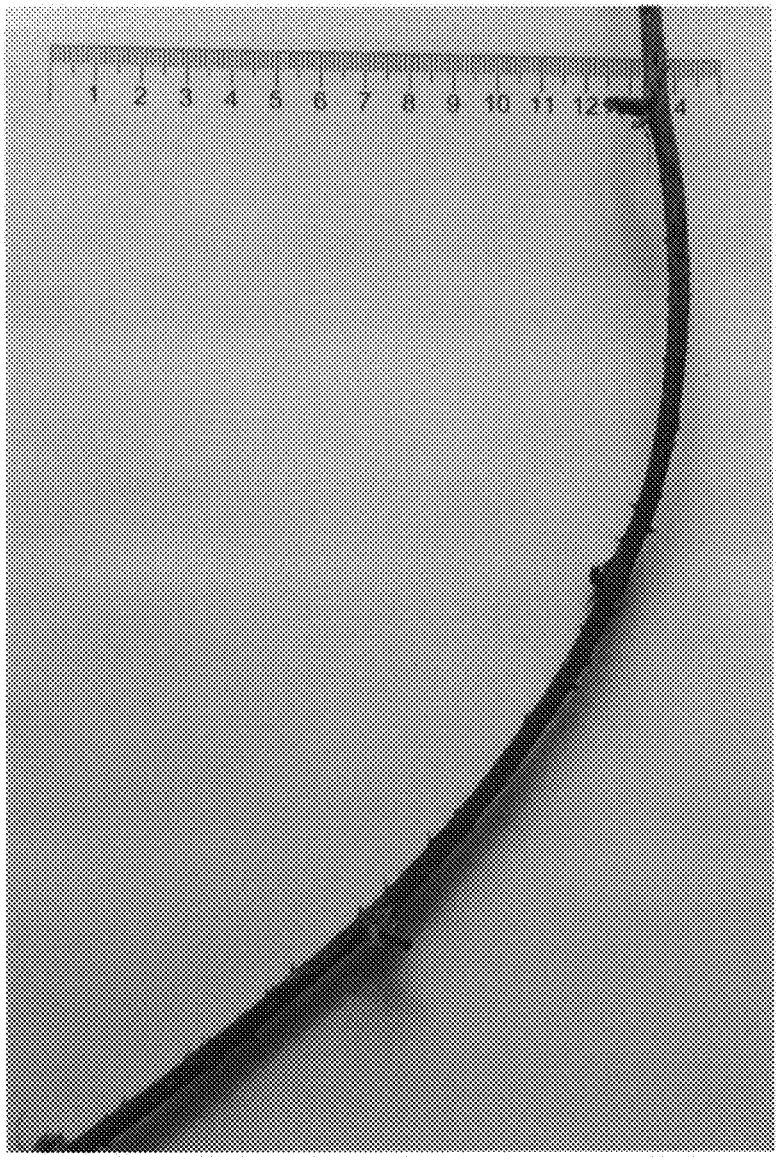
Figure 2:
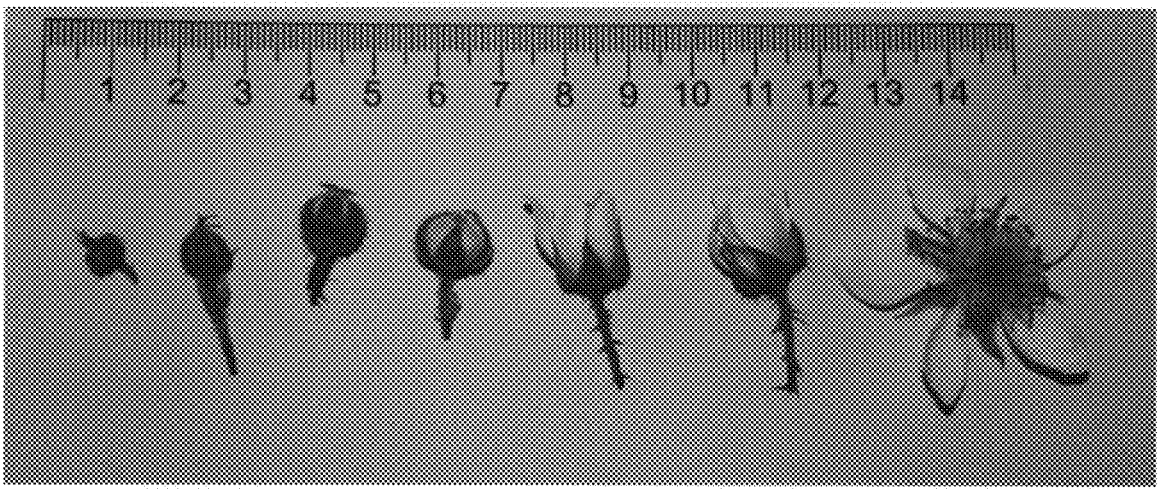

The photograph in FIG. 2 provides a close-up view of flowers of 'FNZ-6VB' in various stages of development.

Figure 3:
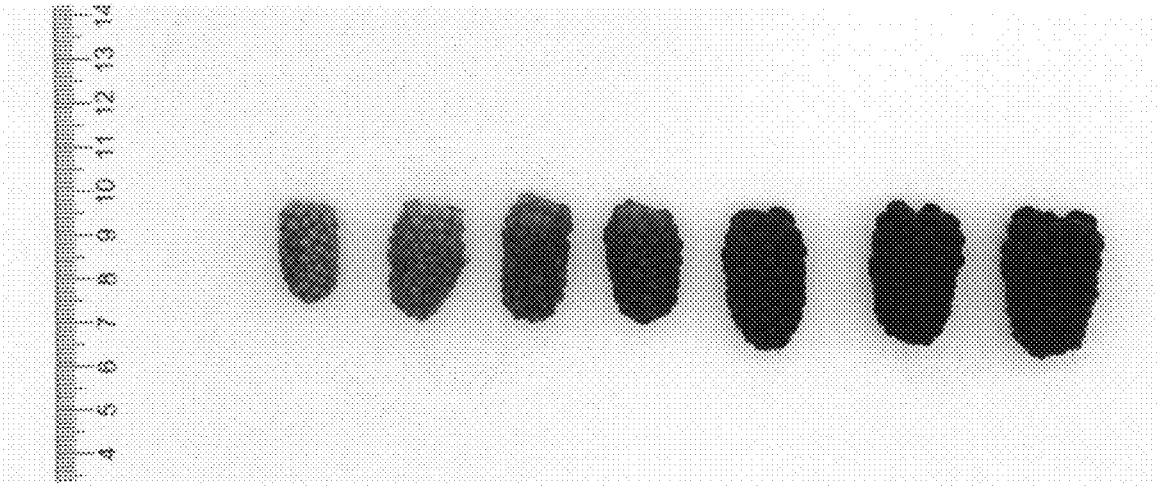

The photograph in FIG. 3 provides a view of berries of 'FNZ-6VB' in various stages of development.

The colors in the photographs are as close as possible with the photographic and printing technology utilized. The colors in the photograph may differ slightly from the color values cited in the detailed botanical description, which accurately describe the colors of the new *Rubus*.

DETAILED BOTANICAL DESCRIPTION OF THE PLANT

The following is a detailed description of plants 2 years in age as grown in a poly tunnel in 22-cm square containers in Faversham, Kent, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Fruit producing perennial.

*Plant habit*.—Spreading.

*Height and spread*.—1.5 to 2.5 m in length and in spread (if not tied up) as a 2 year-old plant as grown in a 10-L container.

*Hardiness*.—This trait has not been fully characterized in a range of cold weather climates but the plants have been successfully grown in central Europe (U. K. Hardiness Zone 9).

*Diseases and pests*.—No resistance or susceptibility to pests or diseases has been observed.

*Environmental stresses*.—No resistance or susceptibility to drought, high temperatures, or water logging has been observed.

*Root description*.—Fibrous and, vigorous.

*Propagation*.—Bud cuttings, cane cuttings or tissue culture.

*Root development*.—An average of 3 weeks to root from a cutting, an average of 3 months to fully develop as a young plant with a cane of 2 m reached in about 10 months.

*Growth rate*.—High vigor.

Cane description:

*Fruit presence*.—On floricanes only.

*Fruiting lateral canes*.—23.33 cm in length, medium in strength (observed on full-grown shoot after picking), slightly glaucous on full grown shoots after picking.

*Cane internode length*.—6.1 cm.

*Young shoots*.—1 or less, emerge in early June, 143A in color with weak anthocyanin 183A, very few glandular hairs.

*Dormant cane*.—1.5 to 2.5 m in length, an average of 5.6 mm in width in mid-section, 59A in color (strong anthocyanin), rounded to angular in cross section, fine in texture, surface matte with thorns; 600 per cane 1 m in length, small-medium in size, 183C in color, attitude to came downward, 1.7 thorns per square cm.

Foliage description:

*Time of vegetative bud burst*.—February in The United Kingdom.

*Leaf arrangement*.—Alternate.

*Leaf division*.—Compound; 3 leaflets.

*Leaf attachment*.—Petiolate.

*Leaf orientation*.—Strongly concave (margins rolled upwards).

*Leaflet shape*.—Round to ovate with elongated point.

*Leaflet base*.—Truncate.

*Leaflet apex*.—Acute.

*Leaflet margins*.—Bi-serrate, lobing absent.

*Leaflet arrangement*.—One terminal and 1 lateral pair.

*Leaflet attachment*.—Primarily sessile.

*Leaflet surface*.—Matt on both surfaces, medium undulation of margin, weak blistering between veins, moderately glossy on upper surface, matt on lower surface.

*Leaflet color*.—137A on upper surface and 138A on lower surface.

*Leaflet size*.—Lateral leaflets; an average of 8.45 cm in length and 5.94 cm in width, length/width ratio 1.4, terminal leaflet; an average of 9.57 cm in length and 7.34 mm in width, length/width ratio 1.3.

*Petioles*.—Round in shape, an average of 4.4 cm in length and 1.9 mm in width, upper surface pigmented with 178B, moderately strong.

*Rachis*.—Round in shape, an average of 1.95 cm between terminal leaflet and lateral leaflets.

*Stipules*.—1 to 2 per petiole, elongated in shape, an average of 1.3 cm in length and 2.5 mm in width, upwards orientation, color 146B on upper surface and 137A on lower surface.

Inflorescence description:

*Blooming period*.—As a floricane; very early season in the United Kingdom.

*Inflorescence*.—Panicle.

*Peduncle*.—Round in shape, color 143C, an average of 3 cm in length and 1.5 mm in width, moderate in strength, spiny surface.

*Pedicels*.—Round in shape, color 143C, an average of 3.8 cm in length and 1.5 mm in width, moderate in strength, spiny surface.

*Flower type*.—Rotate, single.

*Flower number*.—An average of 5.2 (measured at 3$^{rd}$ node from tip of lateral).

*Flower diameter*.—4.18 cm.

*Petals*.—Average of 5, an average of 1.86 cm in length and 1 cm in width, base attenuate, apex acute, entire margin with slightly undulation, glabrous and matte on upper and lower surfaces, NN155C in color on both surfaces.

Fruit description:

*Productivity*.—When grown in substrate; fruiting in second year an average of 450 g/cane with 5 canes per pot.

*Self-fruitfulness*.—Self fruitful.

*Fruit number*.—An average of 6 per lateral cane.

*Fruit size*.—Medium-large, an average of 3.48 cm in length and 2.08 cm in diameter, length/width ratio 1.7.

*Fruit color*.—144B when immature, N34A when maturing, and 203B when mature.

*Fruit shape*.—Oblong.

*Number of duplets/fruit*.—An average of 102.5.

*Fruit surface*.—Medium glossiness.

*Fruit maturity date*.—Very early season on floricanes.

*Seed weight*.—0.008 g/seed.

*Cropping frequency*.—Annually, every 3 weeks during the fruiting season.

*Harvest dates*.—First date approximately June 25th and last harvest date approximately August 2nd as grown in pots in The United Kingdom.

*Flavor*.—Pleasant and sweet when ripe.

*Fruit weight*.—7.4 g/fruit.

*Brix*.—14°.

*Titratable acid*.—1.09 (% as citric acid).

*Fruit firmness*.—Medium firm.

*Shelf life*.—An average of 7 days after picking.

*Market use*.—Fresh fruit.

It is claimed:

1. A new and distinct cultivar of Blackberry plant named 'FNZ-6VB' as herein illustrated and described.

* * * * *